United States Patent
Dumoulin et al.

(10) Patent No.: US 10,694,956 B2
(45) Date of Patent: Jun. 30, 2020

(54) METHOD AND DEVICE FOR MONITORING A BABY FOR INTERACTION

(71) Applicants: Amaury Dumoulin, Neuilly sur Seine (FR); Guillaume Mathias, Paris (FR); Eric Carreel, Meudon (FR)

(72) Inventors: Amaury Dumoulin, Neuilly sur Seine (FR); Guillaume Mathias, Paris (FR); Eric Carreel, Meudon (FR)

(73) Assignee: WITHINGS, Issy les Moulineaux (FR)

( * ) Notice: Subject to any disclaimer, the term of this patent is extended or adjusted under 35 U.S.C. 154(b) by 0 days.

(21) Appl. No.: 14/804,873

(22) Filed: Jul. 21, 2015

(65) Prior Publication Data

US 2016/0015277 A1    Jan. 21, 2016

(30) Foreign Application Priority Data

Jul. 21, 2014 (FR) ...................................... 14 56996

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0004* (2013.01); *A61B 5/02416* (2013.01);
(Continued)

(58) Field of Classification Search
CPC ................ G06K 9/0053; G06K 9/3233; G06T 2207/10024; G06T 2207/10048;
(Continued)

(56) References Cited

U.S. PATENT DOCUMENTS 5,107,845 A *  4/1992  Guern .................... A61B 5/113
                                                        348/143
2007/0288060 A1* 12/2007 Stickney .............. A61B 5/0809
                                                         607/8
(Continued)

FOREIGN PATENT DOCUMENTS

WO   WO 2013164724 A1 * 11/2013  ............. G06T 7/20
WO   WO 2013166341 A1 * 11/2013  ............. G06T 7/408

OTHER PUBLICATIONS

Fang Zhao, et al; *"Remote Measurements of Heart and Respiration Rates for Telemedicine"*; Plos One; vol. 8, Issue 10; Oct. 2013.
(Continued)

*Primary Examiner* — Gary Jackson
*Assistant Examiner* — Jonathan T Kuo
(74) *Attorney, Agent, or Firm* — Miller, Matthias & Hull LLP

(57) ABSTRACT

A method for video evaluation of the heart rate and/or respiratory rate of a baby, in particular under dim or nocturnal conditions, in a device comprising a video camera and a source of infrared light, the method comprising the steps of:
A1—illuminating the baby with the infrared source,
A2—capturing video images of the baby,
B1—determining the position of the baby's head by finding an ellipse forming an outline of the head,
B2—identifying an area of interest centered on a selected ellipse,
C—evaluating, by plethysmographic analysis of the area of interest, the heart rate and/or respiratory rate of the baby, and associated system.

10 Claims, 5 Drawing Sheets

(51) Int. Cl.
*A61B 5/024* (2006.01)
*A61B 5/08* (2006.01)
*A61B 5/11* (2006.01)
*G06T 7/00* (2017.01)
*G06K 9/32* (2006.01)
*G06K 9/00* (2006.01)
*G06T 7/73* (2017.01)
*H04N 7/18* (2006.01)
*G01N 33/00* (2006.01)

(52) U.S. Cl.
CPC .......... *A61B 5/0816* (2013.01); *A61B 5/1128* (2013.01); *A61B 5/7207* (2013.01); *G01N 33/0047* (2013.01); *G06K 9/0053* (2013.01); *G06K 9/3233* (2013.01); *G06T 7/0016* (2013.01); *G06T 7/75* (2017.01); *H04N 7/185* (2013.01); *A61B 2503/04* (2013.01); *A61B 2560/0242* (2013.01); *G06T 2207/10024* (2013.01); *G06T 2207/10048* (2013.01); *G06T 2207/30076* (2013.01); *G06T 2207/30201* (2013.01)

(58) Field of Classification Search
CPC . G06T 2207/30076; G06T 2207/30201; G06T 7/0016; G06T 7/0046; A61B 5/0205; A61B 2503/04; A61B 2560/0242; A61B 5/0004; A61B 5/02416; A61B 5/0816; A61B 5/1128; A61B 5/7207
See application file for complete search history.

(56) References Cited

U.S. PATENT DOCUMENTS

| | | | |
|---|---|---|---|
| 2011/0028802 A1* | 2/2011 | Addison | A61B 5/08 600/301 |
| 2014/0111199 A1* | 4/2014 | Oh | A61B 5/11 324/309 |
| 2014/0155759 A1* | 6/2014 | Kaestle | A61B 5/0077 600/479 |
| 2014/0171059 A1* | 6/2014 | Parker | H04M 1/274533 455/419 |
| 2014/0192135 A1* | 7/2014 | Babineau | H04N 7/181 348/14.02 |

OTHER PUBLICATIONS

Bouaynaya, et al; "A complete system for head tracking using Motion-Based Particle Filter and Randomly Perturbed Active Contour"; article; pp. 1-10; Department of Electrical and Computer Engineering, University of Illinois.

\* cited by examiner

METHOD AND DEVICE FOR MONITORING A BABY FOR INTERACTION

CROSS-REFERENCE TO RELATED APPLICATION

This application claims priority under the Paris Convention to French Patent Application No. 14 56996 filed on Jul. 21, 2014.

FIELD OF THE DISCLOSURE

The present invention relates to video monitoring devices and methods for monitoring a baby, in particular for the purposes of monitoring a baby sleeping in its crib in dim or nocturnal conditions, or in other words in partial or total darkness; the present invention also relates to methods for interaction between a baby and its parent or caregiver.

BACKGROUND OF THE DISCLOSURE

More specifically, the invention relates to a method and device for monitoring certain vital signs of the baby, in particular the heart rate and respiratory rate.

U.S. Pat. No. 8,094,013 discloses a device of this type. However, according to this document a strap must be attached around the baby's body, which is tedious to perform and is not suitable if the baby is already asleep.

WO2013170035 also discloses a device of this type; however, it is necessary to install a monitoring pad under the baby's body, which is not suitable if the baby is already asleep, and the system is ineffective if the baby moves beyond the sensitive area of the pad.

The present invention is intended to overcome at least some of the disadvantages of the prior art.

SUMMARY OF THE DISCLOSURE

To this end, a first general aspect of the invention provides a method for video evaluation of the heart rate and/or respiratory rate of a baby in dim or nocturnal conditions, in a device comprising a video camera and a source of infrared light, the method comprising the steps of:
A1—illuminating the baby with the infrared source,
A2—capturing video images of the baby,
B1—determining the position of the baby's head by detecting edges (borders) forming portions of an ellipse substantially coinciding with the outline of the head,
B2—identifying an area of interest substantially centered on the ellipse,
C—evaluating, by photoplethysmographic analysis of the area of interest, the baby's heart rate and/or respiratory rate.

The method further comprises a step D—of identifying a significant movement of the baby, in which case step C—of photoplethysmographic analysis is suspended; this avoids erroneous results when the baby changes position or makes a significant movement that does not allow the photoplethysmographic analysis to continue correctly.

The method further comprises a step D2—of identifying a return to a stable state where there is no significant movement by the baby (after the movements have stopped), in which case steps B1—and B2—are executed once again, and step C—of photoplethysmographic analysis is reinitialized with the new area of interest determined at step B2—; which allows the method to redetermine the position of the baby's head and to resume the photoplethysmographic analysis.

With these arrangements, a method is provided that requires no contact with the baby to implement it, and can therefore be applied even if the baby is already asleep in its crib. In addition, such a method is compatible with the baby moving, changing position, and turning over; and the device that implements the method has a contactless interaction with the baby, being based on video monitoring and an advantageous analysis of the captured images, and is easy to install.

In various embodiments of the above invention, one or more of the following arrangements may possibly be used.

The images are preferably captured in color and the photoplethysmographic analysis is preferably based on the red component of the video images; as the red component of the video signal provides the most relevant information during dim or nocturnal conditions under infrared light for performing the photoplethysmographic analysis.

A method of image convolution with statistical thresholding is preferably used in step B1—to detect edges or edge segments in the image. The edge segments can thus be extracted from the analyzed image in an effective manner.

In step B1—, candidate ellipses are formed from the identified edge segments, and a selection filter is applied to the candidate ellipses to retain only one selected ellipse coinciding with the outline of the baby's head; this provides a comprehensive and systematic method for extracting candidate ellipses from the edge segments, and for choosing among them the most relevant ellipse that can correspond to the baby's head.

In step C—, to determine the heart rate, a digital filter with passband of 0.75 Hz-3.5 Hz is applied to the light signal spatially averaged over the area of interest, to obtain a filtered signal; this advantageously eliminates the continuous component of the signal as well as all interference signals having a frequency higher than the upper limit of the digital filter, here 3.5 Hz, which is advantageous for extracting the heart rate.

A validity criterion concerning the relevance of the filtered signal is defined, for selectively validating or not validating the heart rate information, the validity criterion being based on the signal-to-noise ratio; whereby the method only delivers the heart rate information if it is reliable, otherwise the heart rate information output is invalidated.

The captured images may be divided into an array of sub-images of identical size; processing can thus be applied to the sub-images successively, requiring less computing power and fewer resources.

Preferably, at step B1—the sub-images having a neutral content, meaning with no significant variation in color or intensity within the area of the sub-image, are eliminated, and after step B2—the sub-images located outside said selected ellipse are eliminated; this avoids processing the sub-images of no interest, and means a shorter time for processing the complete image.

The invention also relates to a device for evaluating the heart rate and/or respiratory rate of a baby in dim or nocturnal conditions, comprising a video camera, a source of infrared light, and a computing unit, wherein the infrared source is configured to illuminate the baby, the video camera is configured to capture video images of the baby, and the computing unit is configured to implement the method as described above.

Advantageously, the device may further comprise a wireless communication interface for transmitting the baby's heart rate and/or respiratory rate data to a remote entity; in this manner, the information about the baby's vital signs can be displayed on the screen of a smartphone at a distance from the crib where the baby is sleeping.

According to a second aspect of the invention, which may be combined with the above aspect or remain independent of the first aspect, a device is provided having the general function of monitoring a baby, and which further comprises a volatile organic compounds sensor (known as a "VOC sensor") which provides an indication of the quality of the air within the room. Such a sensor can detect multiple organic gases, such as butane, propane, octane, methanol, ethanol, propanol, butanol, and even aromatic compounds such as benzene, ethylbenzene, and toluene. The baby monitoring device may record the concentration of organic compounds detected by the sensor over one or more periods of time, and send this information either in real time or in deferred mode to a remote entity such as a smartphone.

A device is thus proposed having the general function of monitoring a baby, comprising a computing unit, a communication interface, and a volatile organic compounds sensor, said computing unit being configured to record the concentration of organic compounds reported by the volatile organic compounds sensor, and to send this information to a remote entity such as a smartphone. Alternatively, the computing unit stores the organic compound concentration data in memory, for transmission at regular intervals to the smartphone. In addition, an alert threshold may be provided in the computing unit of the monitoring device, which allows immediately sending an alert when the VOC concentration exceeds a predetermined threshold, and immediately alerting the smartphone holder.

According to a third aspect of the invention, which may be combined with the above aspects or remain independent of the above aspects, a method for detecting the cries of a baby is provided. Specifically, the computing unit records audio signals from the microphone, and performs digital processing to identify a sound signature characteristic of a crying baby.

A device is thus provided that has the general function of monitoring a baby, comprising a computing unit, a communication interface, and a microphone, said computing unit being configured to analyze the audio signals received from the microphone in order to carry out a spectral or statistical analysis of the audio signal, for the purposes of processing it with an algorithm able to detect a baby's cries and if such are detected to send a high-level alert (SMS or equivalent message) to a remote entity such as a smartphone.

The detection algorithm can be calibrated to reference sound signatures originating, for example, from a general library of signals. The reference sound signatures may also come from previous recordings obtained on the same device, preferably for the same baby when crying. This improves the relevance of the detection, through learning.

A fourth aspect of the invention, which may be combined with the above aspects or be independent of the above aspects, proposes a monitoring device and a method for helping the baby to fall asleep, by controlling an atmospheric lighting and playing soft music. Specifically, the monitoring device comprises a computing unit, a microphone, and a detection function for detecting the heart rate and/or movements of the baby. The detection function can be provided via the video monitoring and the heart rate determination as described in the first aspect of the invention. The detection function may also be provided alternatively or in combination with the above by a sensor in the form of a sheet that detects the baby's movements, this sheet being intended for placement between the baby and the mattress of the bed. The baby's drowsiness phase could be determined as being, for example, when the heart rate slows and becomes more regular with no significant movement of the baby.

A method for guiding the baby's drowsiness phase is thus provided, comprising a step of monitoring certain vital signs such as the baby's heart rate and movement(s), a step of identifying the beginning of the drowsiness phase in which certain vital signs substantially correspond to parameters predetermined as being a drowsiness phase, a step of activating atmospheric lighting of decreasing intensity, and a step of activating atmospheric sound of decreasing intensity. The vital signs are detected, either through video monitoring and in particular the identification of the baby's heart rate and head movements, or through the use of a detection sensor sheet.

A fifth aspect of the invention, which may be combined with the above aspects or be independent of the above aspects, proposes a monitoring device which further comprises a detection sheet to be placed between the baby and the mattress, this sheet being intended to capture the baby's movements, both macroscopic and microscopic. The baby's respiratory rate can thus be determined by analysis and processing of the signal.

A device is thus provided having the general function of monitoring a baby, comprising a computing unit, a microphone, and a detection sheet to be placed between the baby and the mattress in order to capture the baby's movements, the computing unit being adapted to determine the baby's respiratory rate based on audio information captured by the microphone and movement information captured by the detection sheet.

The detection sheet may be formed by a thin air bladder; alternatively this detection sheet may be formed by piezoelectric sensor elements.

In addition, the device may be equipped with a communication interface for transmitting the respiratory rate data to a remote device such as a smartphone.

According to a sixth aspect of the invention, which may be combined with the above aspects or be independent of the above aspects, a method is provided for producing stimuli for the baby that mimic the mother's heartbeats, as sound through a speaker and/or via the detection sheet which can be equipped with an active pneumatic device capable of generating pressure pulses similar to heartbeats.

BRIEF DESCRIPTION OF THE DRAWINGS

Other features, objects, and advantages of the invention will be apparent from reading the following description of an embodiment of the invention, given by way of non-limiting example. The invention will also be better understood by referring to the accompanying drawings, in which.

DETAILED DESCRIPTION

Figure 1:
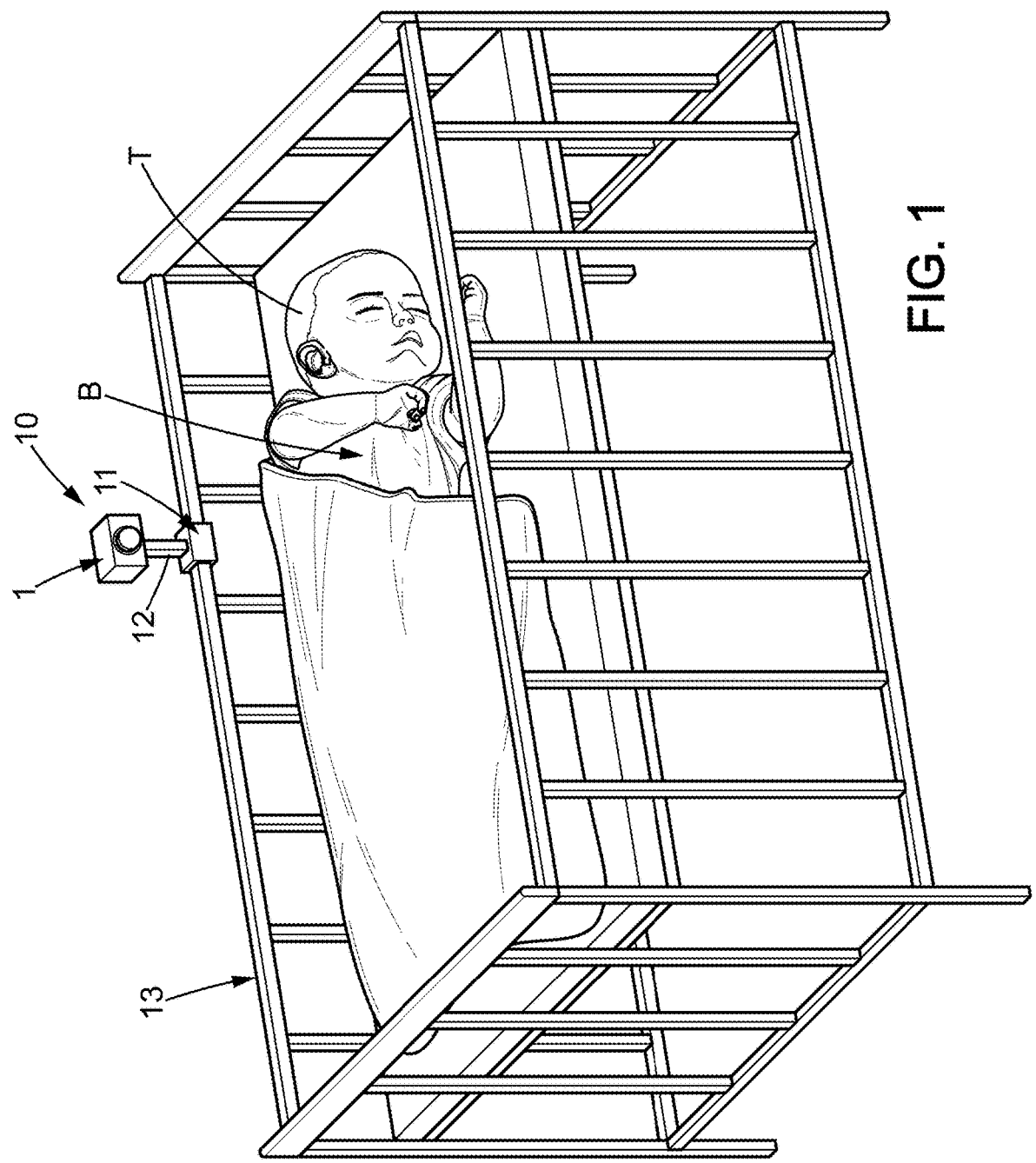
FIG. 1 is a general view of a crib containing a baby to be monitored by a method according to the invention.

FIG. 1 shows a baby B lying in a crib 13. In the context of the invention, baby is understood to mean an infant or child less than 10 years old. We are particularly interested in the case where the baby is placed in the crib for a nap or for the night. Typically, in this configuration, the general lighting in the room will be low or very low, referred to herein as dim or nocturnal conditions providing partial or total darkness.

In the example shown, a video monitoring system, denoted 10, comprises a video monitoring device 1 to be discussed in detail below, a mounting foot 12, and a mounting clamp 11. In the example shown, the mounting clamp is attached to a side rail of the crib or more generally of the bed. Note that in the monitoring assembly, it could also be secured to the crosspiece at the head or the foot of the bed.

Alternatively, the monitoring assembly may also be located elsewhere in the room.

The video monitoring device 1 may be attached to a different support, to a wall, to a bed canopy, etc. However, it is advantageous that the position of the video monitoring device be relatively stable compared to the bed or crib 13.

Figure 2:
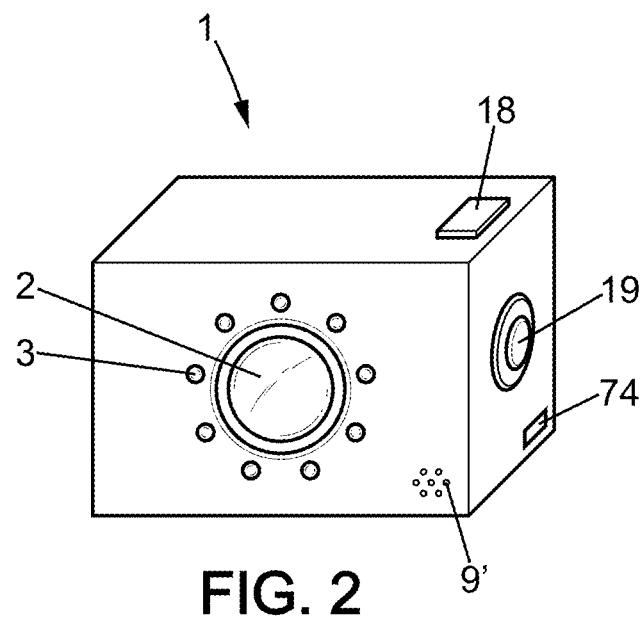
FIG. 2 is a view of the video monitoring device.
Figure 3:
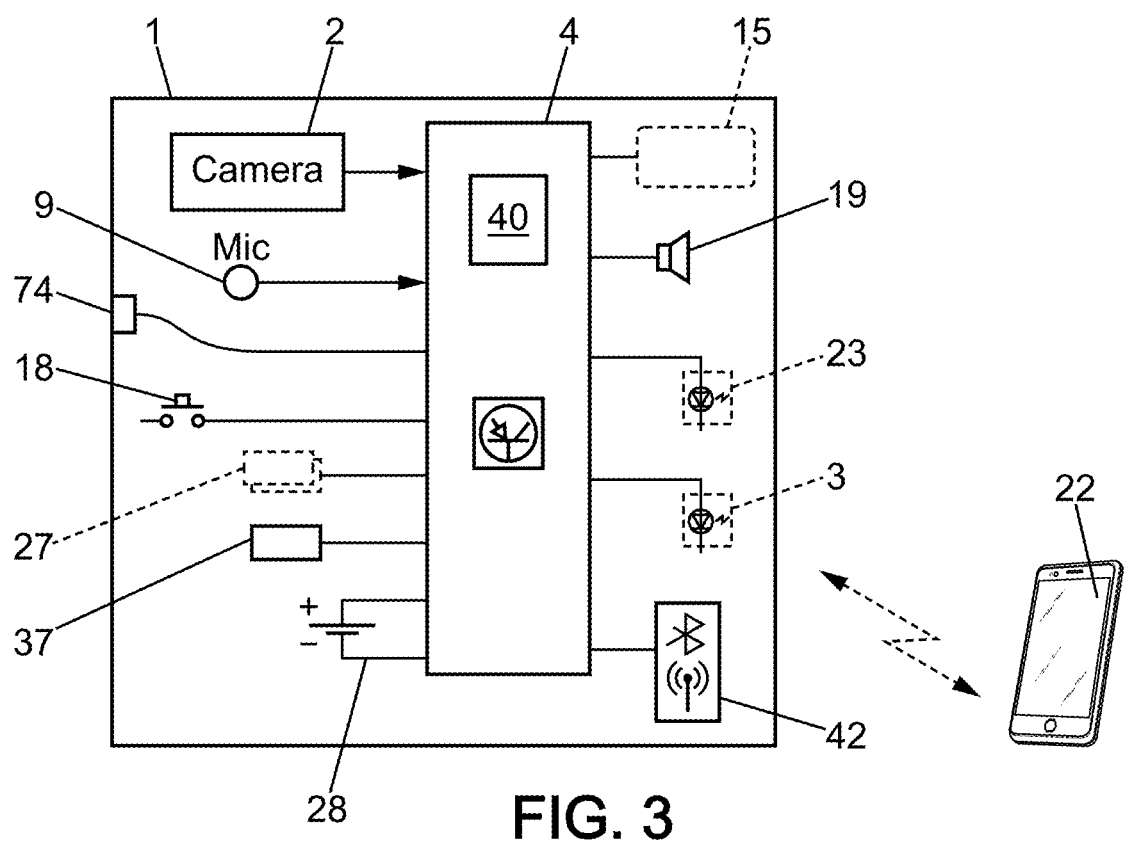
FIG. 3 shows a schematic block diagram of the device of FIG. 2.
Figure 4:
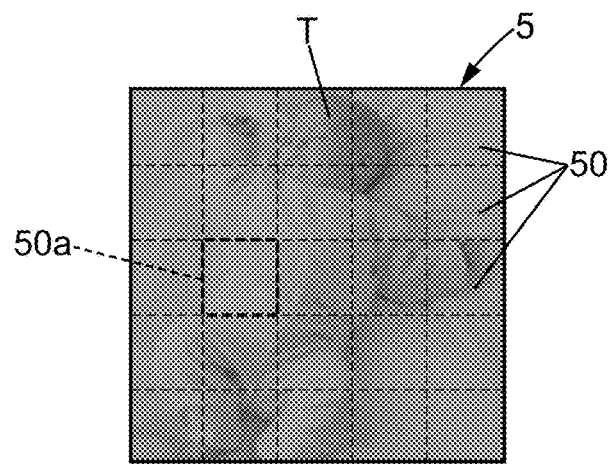
FIG. 4 represents a sample image captured by the camera.
Figure 5:
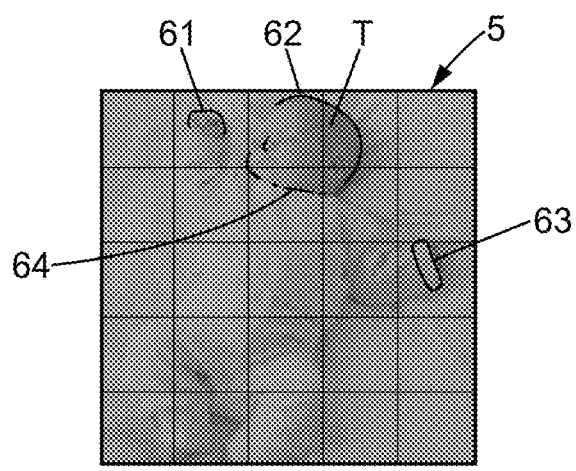
FIG. 5 illustrates the construction of edge segments.
Figure 6:
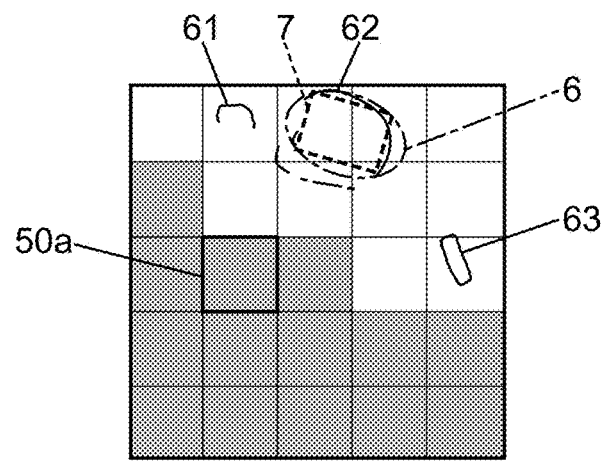
FIG. 6 illustrates the selection of an ellipse and of the area of interest.

As illustrated in more detail in FIG. 2, the video monitoring device 1 comprises a video camera 2, which in the illustrated example, has a wide viewing angle over a solid angle of at least 90° or more (110° or 135°) so that the camera can capture images of the entire relevant area of the crib. In addition, the monitoring device comprises light-emitting diodes 3 (LED) capable of emitting in the infrared band, thus forming a source of infrared light.

In the example shown, the LEDs 3 are arranged all around the camera lens, but could be arranged otherwise with the camera and infrared lighting functions physically separated.

The video monitoring device 1 further comprises a computing unit 4 with a memory 40 as well as a battery 28 or alternatively a power supply unit connecting to the grid.

The video monitoring device 1 preferably also comprises a wireless communication interface 42 configured for exchanging data with a remote entity such as a smartphone 22.

The video monitoring device 1 may further comprise a microphone 9 for capturing sound, and a sound generator in the form of a small speaker 19.

In addition, there may be a light source 23 for dim atmospheric lighting whose intensity can be controlled by the monitoring device, an air quality sensor 37, and auxiliary sensors 27 for example for sensing temperature and/or humidity and/or air quality.

The video monitoring device 1 may further comprise one or more buttons 18, intended to be operated by a user (for example to configure the device, turn it on and turn it off) as well as a small display 15 for displaying states or parameters of the device (in which case the buttons 18 may be touch-sensitive).

The device may comprise a connector 74, and holes 9' near the bottom of the front face to improve pickup by the microphone.

Advantageously according to the invention, the camera 2 periodically captures video images 5 of the baby B. The image capture frequency will be a few hertz or tens of hertz, preferably higher than 8 Hz. It should be noted that in the context of the invention the same camera is used to capture images in daylight and images in the dark.

An optical filter may be provided having two positions, i.e. a day position and a night position.

The device controls excitation of the infrared LEDs 3 either continuously or at times coinciding and consistent with the capture of images. The infrared LEDs are arranged so as to substantially illuminate the entire solid angle of view of the camera.

Advantageously according to this version, the method for image processing and analysis will seek to determine the position of the baby's head T.

To do so, a step of the method, denoted B1—, consists of detecting edges or edge segments in one or more successive images captured by the camera.

The images 5 are captured in color in the example illustrated, and in dim or dark conditions under infrared light. One may preferably choose to work specifically with the red component of each image (among the components red, green and blue of the 'RGB' color space). It is also possible to work with the green component or a configured mix of colors.

For each image, spatial convolution with statistical thresholding is performed, or calculation of the correlation to the mean of the red component or of the configured mix of colors. This allows identifying and memorizing the curve portions 61,62,63,64 where the spatial gradient of the signal is the highest, corresponding in practice to edge segments within the image.

Identification of these edge segments can be confirmed by sequential analysis of several successive images; if similar edge segments are found at the same location in these multiple images, then the determination is confirmed.

Otherwise it may concern a macroscopic movement of the baby, a case which will be explained below.

When sequential analysis of several successive images has confirmed the presence of several edge segments, we proceed to the next step in which several edge segments are associated and together they are compared to an elliptical shape (ellipse) with which said several edge segments might match.

A relevance criterion is established for quantifying the correspondence of the combined edge segments 62,64 with the candidate ellipse.

Of course, if a continuous outline is found which forms a circle or a closed ellipse in the analyzed image, then the relevance criterion will assume the maximum value; but in practice often the image analysis only detects portions of the candidate ellipse, and the ellipse must be reconstructed and assigned a relevance criterion value.

This step, referenced B2—, may in addition identify a plurality of candidate ellipses, in which case a selection filter is applied to the candidate ellipses to choose only one selected ellipse 6 coinciding with the outline of the baby's head T. This filter may use the size of the ellipse, the ratio of its major axis to minor axis, and also the proportion of the outline actually found in the previous step.

Note that the method presented could also work for detecting two (or more) baby heads in a crib containing two babies, in which case the filter would not be limited to identifying a single candidate ellipse but two ellipses.

In the typical case of one head to be detected, the selection of such a selected ellipse 6 allows eliminating from the subsequent analysis all image areas outside of the ellipse, and defining an area of interest centered on the ellipse.

Once the area of interest has been determined, and subject to the baby making no significant movements (see below), then the step denoted C—of the method is carried out, this step corresponding to a photoplethysmographic analysis intended to determine vital signs of the baby, particularly the heart rate HR but also the respiratory rate RR.

Advantageously, one can determine a first area of interest 7 for evaluating the heart rate, and a second area of interest that may be distinct from the first, for evaluating the respiratory rate.

Figure 7:
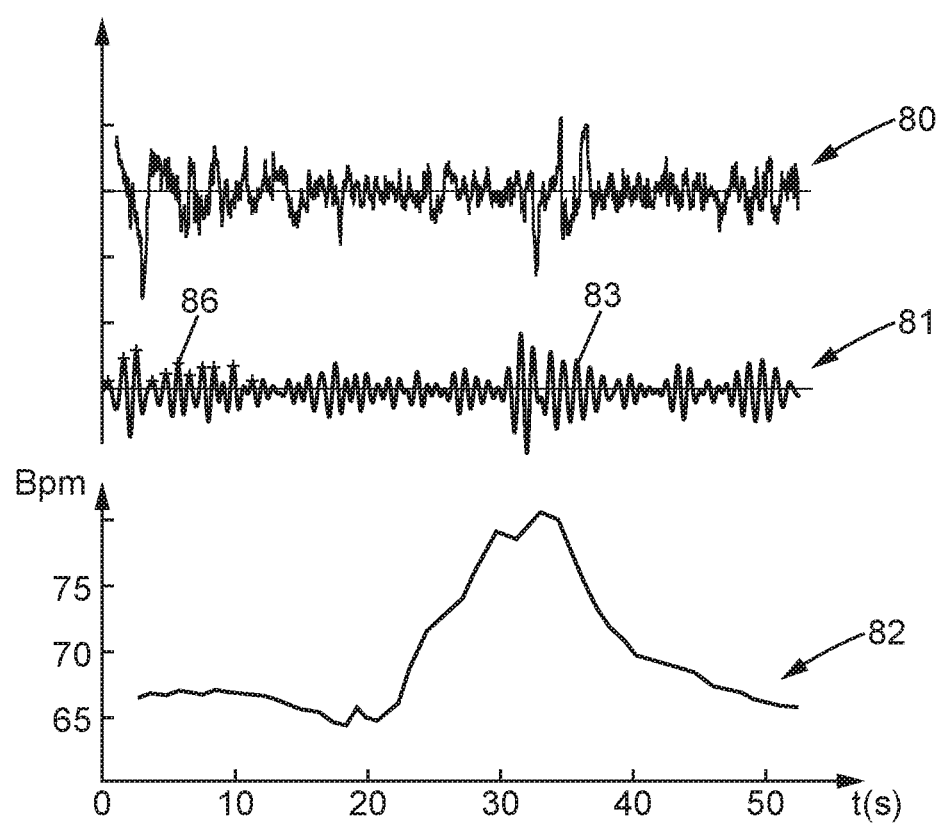
FIG. 7 illustrates an example of a filtered signal.

Preferably, for the heart rate determination, first there is applied to the light signal spatially averaged over the first area of interest, a sliding-window based offset calculation to eliminate the continuous component of the signal. This results in a signal denoted 80 in FIG. 7, which remains relatively noisy but no longer contains a continuous component.

Next, a digital filter with passband of 0.75 Hz-3.5 Hz is applied to the signal 80 in order to obtain a filtered signal 81. This eliminates spurious signals outside the frequency band of interest.

A peak detection step is then applied to the resulting filtered signal 81. This processing is intended to find the peaks 86 (only the first ones are indicated by crosses in FIG. 7).

The time interval between each consecutive peak 86 allows calculating the heart rate as illustrated in curve 82.

Optionally, a validity criterion relating to the relevance of the filtered signal 8 may be defined, to be used for selectively validating or not validating the heart rate information. This validity criterion may be based on the signal-to-noise ratio (S/N) of the signal 81.

A filtered and corrected signal is denoted 83.

If the heart rate value from step C—satisfies the validity criterion, this value may be stored in memory and/or transmitted to a remote device 22 such as a smartphone connected by wireless link to the monitoring device 1.

Step C—is carried out almost continuously, repeating periodically, for example obtaining a measurement every 5 seconds or every 10 seconds, knowing that to obtain each measurement, when appropriate, the device can increase the rate at which it captures images in the area of interest.

In parallel to step C—, the method monitors that the baby is remaining substantially motionless, or in other words that the edge segments identified in step B1—remain substantially stable.

A special case is handled by the method according to the invention: when there is significant (macroscopic) movement of the baby. In this case, the baby's head moves, and the head's position must be determined again.

Detection of a significant movement of the baby (step D—) can be achieved by analysis of the position of the edge segments and their evolution over successive images. Additionally or alternatively, the information provided by the microphone 9 can also be used, because a macroscopic motion of the baby will generate audio signals received by the microphone.

Those skilled in the art understand that a plethysmographic analysis cannot yield valid results when the baby is making significant movements.

However, it is arranged that the evolution of these movements are monitored (the steps denoted D—, D2—) in order to identify a return to a stable state where there is no significant movement by the baby, in which case steps B1—and B2—are performed again, step C—of photoplethysmographic analysis being repeated with the new area of interest 7 established in step B2—.

Therefore, advantageously, no particular precaution is required to focus on the head of the baby, since the systems re-determine the position of the head after each macroscopic movement of the baby. The photoplethysmographic analysis (C—) is automatically suspended during movement(s) and resumed after return to a stable position of the baby.

The abovementioned processing may be performed on the entire captured image 5. However, as a variant, the image may be subdivided to limit the computation resources required and the memory required. For example, the captured image 5 can be divided into an array of sub-images 50, each sub-image 50 being the same size to facilitate processing. In the illustrated example, the captured image is divided into 5×5 sub-images.

This has the advantage that certain images of flat or neutral content 50a (meaning with no significant variation in color or intensity over the area of the sub-image) can be eliminated during the edge detection in step B1—. One criterion for eliminating the sub-images 50 of no interest can be based on a low light intensity and/or a low variation in the analyzed area.

It is also possible to eliminate, after choosing the selected ellipse 6, all sub-images with flat or neutral content 50a located outside the ellipse or even outside the area of interest 7.

Of course, if the method discovers edge segments overlapping multiple sub-images, new processing is performed on the combined sub-images in question.

Note that the first area of interest, for the heart rate, preferably concerns the baby's forehead, while for the second area of interest, for the respiratory rate, the entire face can be part of the area of interest.

Figure 8:
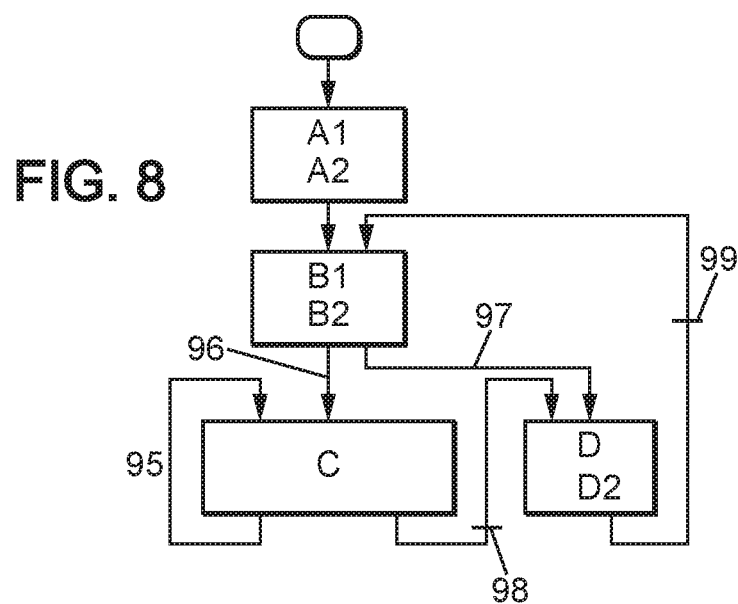
FIG. 8 shows a flowchart illustrating the method.

Now referring to FIG. 8, since steps B1—and B2—have identified an area of interest, the transition 96 initializes the plethysmographic analysis (C—), and this is repeated (denoted 95) as long the baby is not moving. If the baby moves, then the plethysmographic analysis is suspended 97,98 and the step of monitoring the macroscopic movements (step D—) puts the plethysmographic process on hold until a stable state is restored (step D2—), illustrated by transition 99. Then the method restarts steps B1—and B2—, and then proceeds to step C—.

Advantageously, the plethysmographic analysis can be preformed even if the baby's head is viewed from behind.

Advantageously according to the invention, even if the baby's position changes a lot during sleep, and even if the baby turns over, detection of the position of the head by the proposed method allows continuously monitoring the baby's vital signs.

It should also be noted that the device installation does not require any special precautions, as automatic detection of the baby's head is possible even if the framing by the camera is not perfect relative to the crib.

For the determination of the respiratory rate, step C—must be adapted, for example with the passband limits of the digital filter being three times lower.

The analysis criteria for the filtered signal for detection of the respiratory rate, as well as the validation criteria for the resulting signal, rely in this case on an iteration mechanism.

It should be noted that the method for detecting the baby's head as disclosed above can also function in the daytime under natural lighting, and not only under dark illumination conditions.

Furthermore, in the example illustrated, a single camera CCD allows detection of day and night; according to a possible variant, however, the video monitoring device comprises a conventional camera CCD for daylight viewing, and a thermometric or thermal infrared camera for night viewing.

In a complementary aspect, the video monitoring device 1 further comprises a volatile organic compounds sensor 37

(known as a VOC sensor). Such a sensor can detect several organic gases, such as butane, propane, octane, methanol, ethanol, propanol, butanol, and even aromatic compounds such as benzene, ethylbenzene, and toluene. The baby monitoring device may record the concentration of organic compounds during one or more periods of time, and send this information either in real time or in deferred mode to the smartphone 22.

The VOC sensor 37 in question is an ion detector using photoionization of the molecules in an air sample collected in the room where the baby's crib is located. It thus provides a level of organic compounds which combines all the organic compounds present.

According to a complementary aspect, the microphone 9 included in the device 1 continuously analyzes the ambient noise. The dynamics and energy of the signal are observed and when they exceed some adaptive thresholds, crying recognition function begins.

This mechanism preferably uses short sequences (10 to 100 ms) and performs an advanced spectral analysis. From this information, a classifier calculates the probability that the sequence comes from crying. For this purpose, the computing unit 4 stores sound signatures typical of baby cries in spectral form (these are reference values).

Figure 9:
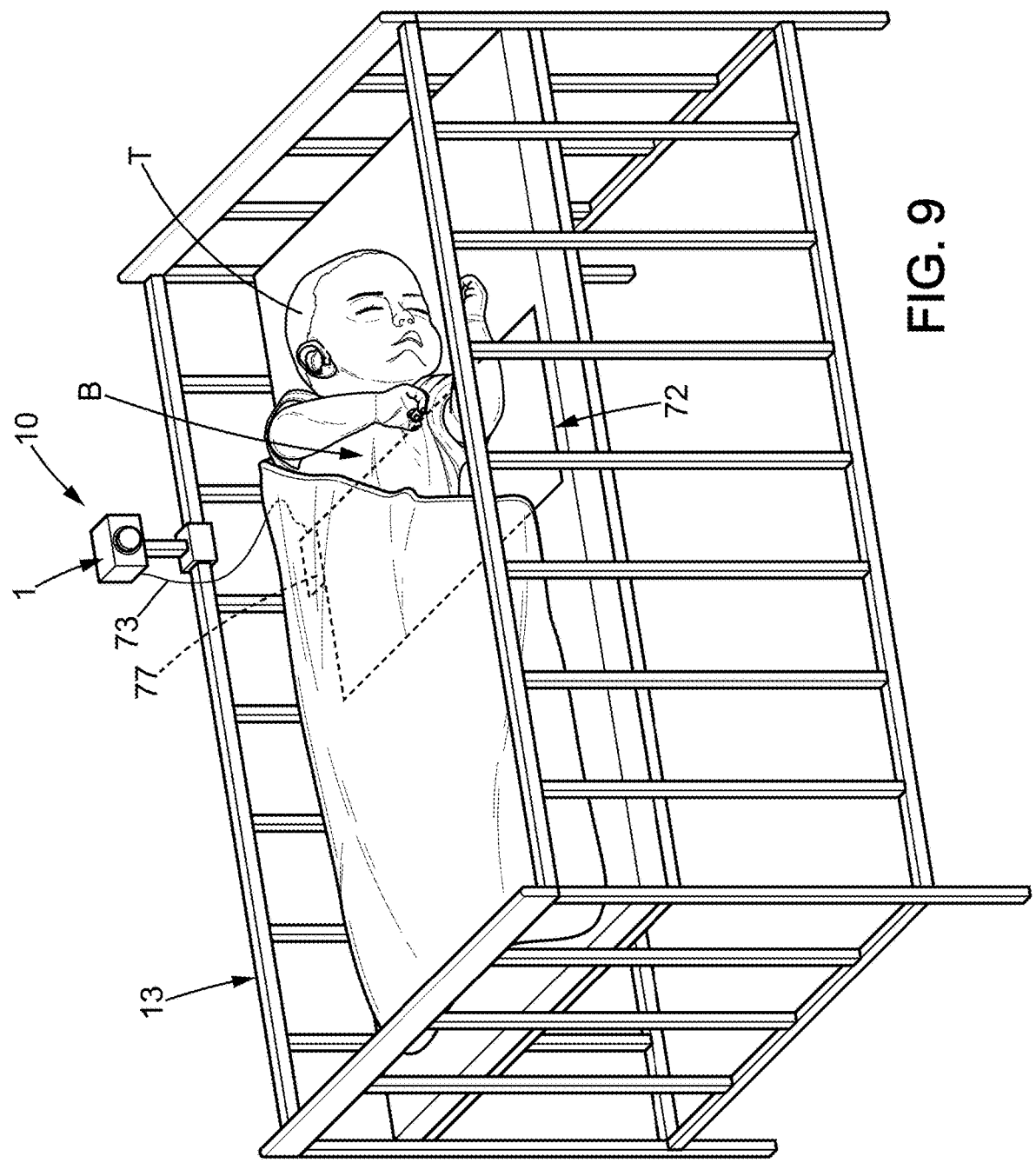
FIG. 9 illustrates a variant of the monitoring device with a detection sheet.

In addition, a detection sheet 72 may be provided that acts as a motion sensor, as shown in FIG. 9. This detection sheet 72 is installed on the mattress and the baby B is placed above it, in other words the detection sheet 72 is placed between the baby B and the mattress. The detection sheet may comprise a signal conditioning interface 77 and is connected to the monitoring device 1 by a flexible link 73, either electrical or pneumatic or a combination. This link 73 is connected to the device via the connector 74. The signal conditioning may be performed by the conditioning interface 77 or even directly wholly or in part by the monitoring device itself.

In the example illustrated, the detection sheet is formed by a thin air bladder, which allows detecting the baby's movements by ballistography. Alternatively, the detection sheet can be also formed by a plurality of piezoelectric or piezoresistive sensors.

In the case where the detection sheet 72 is formed by an air bladder, there may be an air pump (not shown) configured to generate an average measured pressure in the sheet and to generate pneumatic pulses that are used to replicate, for the baby, pulses similar to the mother's heartbeats felt by the baby during pregnancy.

Advantageously in an optional aspect of the device, the computing unit 4 may be configured to detect the beginning of a drowsiness phase of the baby B, for example by monitoring the heart rate and/or monitoring the respiratory rate and/or monitoring the movements of the baby.

To help the baby fall asleep more quickly and more easily, atmospheric lighting is provided by the atmospheric lighting means 23 and soft music through the speaker 19, both of them preferably decreasing in intensity.

To trigger the light and sound sequence, the beginning of the drowsiness phase can be detected by video determination of the heart rate as explained above. When the heart rate 82 slows and becomes more regular, then the control unit 4 triggers the light and sound sequence.

According to an advantageous aspect, there may be a particular sound sequence that mimics the mother's heartbeats as heard by the baby during pregnancy.

Alternatively, the computing unit uses not only the heart rate information but also the respiratory rate information detected for example by means of the microphone 9 and/or of said detection sheet 72. The computing unit 4 may also use video detection of movements of the baby's head T by means of the edge detection method as explained above.

When the computing unit 4 has triggered the sound and light sequence to assist with falling asleep and the baby starts to move about or to cry, then the sequence can be extended or restarted at the beginning.

If the sound and light sequence comes to an end with no change in the heart rate and with no movement of the baby, then the monitoring device turns the atmospheric lighting completely off and switches to night monitoring mode.

According to a particular aspect, based on the selected area of interest (position of the head), the video monitoring device can store in memory a plurality of images of the baby's face, taken at intervals spaced somewhat apart to form a slideshow of the change and growth of the baby.

According to a particular aspect, the video monitoring device can be configured to take larger images than only the baby's crib, which allows generating alerts for the parent and/or caregiver by sending complete images of the room where the crib is located and based on detection of movement, displaying the image of the person(s) present with the baby.

In a particular aspect, the video monitoring device can save the highlights of the day and/or night, in other words it can save images of events which occurred earlier; for example, based on detection of movement near the baby, saving images and audio whenever someone enters or leaves the room, and based on detection of crying, saving images and audio whenever the baby starts to cry, whenever there is a significant change in environmental parameters, whenever the baby smiles, etc.

According to a particular aspect, the video monitoring device can generate an alert sent to a remote device such as a smartphone or other device, upon detection of abnormal conditions such as environmental parameters exceeding preset thresholds, an unusually quiet or unusually restless environment, movement, pollution detection, etc.

Lastly, according to a particular aspect, the video monitoring device can be equipped with a two-way simultaneous audio connection, in other words a full-duplex connection, which allows the parent(s) and baby to exchange words or sound signals truly at the same time.

The invention claimed is:

1. A method for video evaluation of the heart rate and/or respiratory rate of a baby in dim or nocturnal conditions, in a device comprising a video camera having a wide viewing angle of at least 90° and a source of infrared light, the method comprising the steps of:
   A1—illuminating the baby with the infrared source,
   A2—capturing video images of the baby,
   B1—determining the position of the baby's head by detecting edge segments forming separate curved portions of an ellipse coinciding with the outline of the head,
   B2—identifying an area of interest centered on the ellipse,
   C—evaluating, by photoplethysmographic analysis of the area of interest, the heart rate and/or respiratory rate of the baby,
   D—identifying a macroscopic movement of the baby, in which case step C—of photoplethysmographic analysis is suspended,
   D2—identifying a return to a stable state where there is no macroscopic movement by the baby, in which case steps B1—and B2—are executed once again, step C—of photoplethysmographic analysis being resumed with the new area of interest determined in step B2—.

2. The method according to claim 1, wherein the images are captured in color and the photoplethysmographic analysis is based on the red component of the video images.

3. The method according to claim 1, wherein at step B1—, a method of image convolution with statistical thresholding is used to find edges or edge segments in the image.

4. The method according to claim 1, wherein at step B1—, candidate ellipses are formed from the identified edge segments, and a selection filter is applied to the candidate ellipses to retain only one selected ellipse coinciding with a likely outline of the baby's head.

5. The method according to claim 1, wherein in step C—, a digital filter with passband of 0.75 Hz-3.5 Hz is applied to the light signal spatially averaged over the area of interest, to obtain a filtered signal.

6. The method according to claim 5, wherein a validity criterion concerning the relevance of the filtered signal is defined, for selectively validating or not validating the heart rate information, the validity criterion being based on the signal-to-noise ratio of the filtered signal.

7. The method according to claim 1, wherein the captured images are each divided into an array of sub-images of identical size.

8. The method according to claim 7, wherein at step B1—the sub-images having a neutral content, meaning with no variation in color or intensity within the area of the sub-image, are eliminated, and after step B2—the sub-images located outside said ellipse are eliminated.

9. A device for video evaluation of the heart rate and/or respiratory rate of a baby in dim or nocturnal conditions, comprising a video camera having a wide viewing angle of at least 90°, a source of infrared light, and a computing unit, wherein the infrared source is configured to illuminate the baby, the video camera is configured to capture video images of the baby, and the computing unit is configured to:
  A1—illuminating the baby with the infrared source,
  A2—capturing video images of the baby,
  B1—determining the position of the baby's head by detecting edge segments forming separate curved portions of an ellipse substantially coinciding with the outline of the head,
  B2—identifying an area of interest centered on the ellipse,
  C—evaluating, by photoplethysmographic analysis of the area of interest, the heart rate and/or respiratory rate of the baby,
  D—identifying a macroscopic movement of the baby, in which case step C—of photoplethysmographic analysis is suspended, and
  D2—identifying a return to a stable state where there is no macroscopic movement by the baby, in which case steps B1-B2 are executed once again, step C—of photoplethysmographic analysis being resumed with the new area of interest determined in step B2—.

10. The device according to claim 9, comprising a wireless communication interface for transmitting the heart rate and/or respiratory rate data of the baby to a remote entity.

* * * * *